US009283255B2

(12) United States Patent
Li et al.

(10) Patent No.: US 9,283,255 B2
(45) Date of Patent: Mar. 15, 2016

(54) COMPOSITIONS AND METHODS FOR THE PREVENTION AND TREATMENT OF RED BLOOD CELL COAGULATION

(75) Inventors: Ming Li, New Territories (HK); Xiaoli Lin, Jin Hua Zhejiang Province (CN)

(73) Assignee: GENEREX PHARMACEUTICALS, INC., George Town (KY)

( * ) Notice: Subject to any disclaimer, the term of this patent is extended or adjusted under 35 U.S.C. 154(b) by 0 days.

(21) Appl. No.: 13/377,489

(22) PCT Filed: Jun. 11, 2010

(86) PCT No.: PCT/IB2010/001415
§ 371 (c)(1),
(2), (4) Date: Dec. 9, 2011

(87) PCT Pub. No.: WO2010/143061
PCT Pub. Date: Dec. 16, 2010

(65) Prior Publication Data
US 2012/0082741 A1    Apr. 5, 2012

Related U.S. Application Data

(60) Provisional application No. 61/187,905, filed on Jun. 17, 2009, provisional application No. 61/186,709, filed on Jun. 12, 2009.

(51) Int. Cl.
| *A61K 36/00* | (2006.01) |
| *A61K 31/56* | (2006.01) |
| *A61K 31/565* | (2006.01) |
| *A61K 31/7028* | (2006.01) |
| *A61K 31/7032* | (2006.01) |
| *A61K 31/7034* | (2006.01) |
| *A61K 36/23* | (2006.01) |
| *A61K 36/73* | (2006.01) |

(52) U.S. Cl.
CPC .............. *A61K 36/00* (2013.01); *A61K 31/56* (2013.01); *A61K 31/565* (2013.01); *A61K 31/7028* (2013.01); *A61K 31/7032* (2013.01); *A61K 31/7034* (2013.01); *A61K 36/23* (2013.01); *A61K 36/73* (2013.01)

(58) Field of Classification Search
None
See application file for complete search history.

(56) References Cited

U.S. PATENT DOCUMENTS

| 5,589,154 | A   | 12/1996 | Anderson |
| 5,595,743 | A   | 1/1997  | Wu |
| 2001/0055630 | A1 | 12/2001 | Castillo et al. |
| 2002/0068098 | A1 | 6/2002  | Babish et al. |
| 2003/0180395 | A1 | 9/2003  | Bueter |
| 2005/0064048 | A1* | 3/2005 | Li et al. ................. 424/725 |
| 2008/0070826 | A1 | 3/2008  | Selby, III |
| 2008/0260704 | A1 | 10/2008 | Riordan et al. |
| 2009/0022827 | A1 | 1/2009  | Li et al. |

FOREIGN PATENT DOCUMENTS

| CN | 1069629       | 3/1993  |
| CN | 1279970       | 1/2001  |
| CN | 1437973       | 8/2003  |
| CN | 1515311       | 7/2004  |
| CN | 1558769       | 12/2004 |
| CN | 1682788       | 10/2005 |
| CN | 1708313       | 12/2005 |
| CN | 101040901     | 9/2007  |
| CN | 101091751     | 12/2007 |
| CN | 101099770     | 1/2008  |
| CN | 101125171     | 2/2008  |
| CN | 101274012     | 10/2008 |
| CN | 101406537     | 4/2009  |
| JP | 2002-255804   | 9/2002  |
| JP | 2003-342190   | 12/2003 |
| JP | 2006-347967   | 12/2006 |
| JP | 2007-204447   | 8/2007  |
| JP | 2008-007417   | 1/2008  |
| JP | 2008-074801   | 4/2008  |
| KR | 100718602     | 5/2007  |
| KR | 20090020279   | 2/2009  |
| WO | WO-02/09720   | 2/2002  |
| WO | WO-02/078685  | 10/2002 |
| WO | WO-03/043645  | 5/2003  |
| WO | WO-2004/052381 | 6/2004 |
| WO | WO-2005/034958 | 4/2005 |
| WO | WO-2006/054370 | 5/2006 |
| WO | WO-2007/048352 | 5/2007 |
| WO | WO-2007/048353 | 5/2007 |
| WO | WO-2007/049088 | 5/2007 |
| WO | WO-2007/049089 | 5/2007 |
| WO | WO-2007/106049 | 9/2007 |
| WO | WO-2008/144706 | 11/2008 |
| WO | WO-2010/143058 | 12/2010 |
| WO | WO-2010/143059 | 12/2010 |
| WO | WO-2010/143061 | 12/2010 |
| WO | WO-2010/143062 | 12/2010 |

(Continued)

OTHER PUBLICATIONS

Zeng et al. Phytotherapy Research, vol. 12, 146-148 (1998).*
"Diagnosis of Diabetes". Internet Archive Date: Feb. 28, 2005 [Retrieved from internet on:May 18, 2013]. Retrieved from the Internet: <URL: http://web.archive.org/web/20050228073517/ http://diabetes.niddk.nih.gov/dm/pubs/diagnosis/>.*
Dong, H., et al., "Effects of Tannins from Geum japonicum on the Catalytic Activity of Thrombin and Factor Xa of Blood Coagulation Cascade," J. Nat. Prod., Oct. 1998, vol. 61, No. 11, pp. 1356-1360.
International Preliminary Report on Patentability received for PCT/ IB2010/001410 mailed Dec. 12, 2011.
International Preliminary Report on Patentability received for PCT/ IB2010/001412 mailed Dec. 12, 2011.

(Continued)

*Primary Examiner* — Amy L Clark
(74) *Attorney, Agent, or Firm* — Foley & Lardner LLP

(57) ABSTRACT

A pharmaceutical composition for inhibiting mammalian red blood cell coagulation is disclosed. The composition comprises an effective amount of *Geum japonicum*'s organic extract and a pharmaceutically acceptable carrier.

11 Claims, 1 Drawing Sheet

(56) References Cited

FOREIGN PATENT DOCUMENTS

| WO | WO-2010/143063 | 12/2010 |
|----|----------------|---------|
| WO | WO-2010/143065 | 12/2010 |

OTHER PUBLICATIONS

International Preliminary Report on Patentability received for PCT/IB2010/001415 mailed Dec. 12, 2011.
International Preliminary Report on Patentability received for PCT/IB2010/001416 mailed Dec. 12, 2011.
International Preliminary Report on Patentability received for PCT/IB2010/001418 mailed Dec. 12, 2011.
International Preliminary Report on Patentability received for PCT/IB2010/001426 mailed Dec. 12, 2011.
International Search Report received for PCT/IB2010/001415 mailed Oct. 21, 2010.
International Search Report received for PCT/IB2010/001410 mailed Nov. 11, 2010.
International Search Report received for PCT/IB2010/001412 mailed Nov. 11, 2010.
International Search Report received for PCT/IB2010/001416 mailed Nov. 11, 2010.
International Search Report received for PCT/IB2010/001418 mailed Nov. 11, 2010.
International Search Report received for PCT/IB2010/001426 mailed Nov. 11, 2010.
Li, J., "Studies on Bioactive Constituents with Myogenesis and Angiogenesis Activity from Geum Japonicum Thunb" Vax. Chinese F. Bolle, Chinese Doctoral Dissertation & Master's Thesis, Medicine and Health Sciences, Jan 2007, 41 pages. (English abstract provided).
Liu, H., et al., "Fatty Acid Synthase Inhibitors from *Geum japonicum* Thunb. var. Chinese," Chemistry & Biodiversity, Mar. 24, 2009, vol. 6, Issue 3, pp. 402-410.
Ming, D.S., et al. "Research Progress in Chemical Constituents and Biological Activities of *Geum* Species," Acta Pharmaceutica Sinica, 2000, vol. 35, No. 7, pp. 552-558.
Yoshiki, K., et al. "Antitumor agents, 129.1 Tannins and Related Compounds as Selective Cytotoxic Agents," Journal of Natural Products, Aug. 1992, vol. 55, No. 8, pp. 1033-1043.
Zeng, F., et al., "The Anticoagulant Effects of Geum japonicum Extract and its Constituents," Phytotherapy Research, Mar. 1998, vol. 12, pp. 146-148.
Extended Search Report issued in European Application No. 10785823.5 dated Nov. 8, 2012 (12 pages).
Extended Search Report received in European Application No. 10785819.3 dated Nov. 8, 2012 (10 pages).
Extended Search Report received in European Application No. 10785820.1 dated Nov. 13, 2012 (7 pages).
Extended Search Report received in European Application No. 10785822.7 dated Nov. 8, 2012 (9 pages).
International Preliminary Report on Patentability issued for PCT/IB2010/001418 mailed Nov. 22, 2012 (7 pages).
Kang, Soon Ah et al., "Antiinflammatory Activity of the Medicinal Plant Geum Japonicum," Nutritional Sciences, vol. 9, No. 2, (May 1, 2006), pp. 117-123.
Li, Ming et al., "Repair of Infarcted Myocardium by an Extract of Geum japonicum with Dual Effects on Angiogenesis and Myogenesis," Clinical Chemistry, vol. 52, No. 8, (Aug. 1, 2006), pp. 1460-1468.
Myeong-Sim, Ji et al., "Anticoagulant 1,2,3,4,6-pentagalloyl-beta-D-glucopyranos e isolated from geranium (*Pelargonium inquinans* Ait)," Archives of Pharmacal Research, vol. 28, No. 9, (Sep. 2005), pp. 1037-1041.
Samuels, Noah, "Herbal remedies and anticoagulant therapy," Thrombosis and Haemostasis, vol. 93, No. 1 (Jan. 1, 2005), pp. 3-7.
Somova, Lo et al., "Cardiovascular, Antihyperlipidemic and Antioxidant Effects of Oleanolic and Ursolic Acids in Experimental Hypertension," Phytomedicine, vol. 10, No. 2-3, (Jan. 1, 2003), pp. 115-121.
Xie, Yi-Wu et al., "Role of Nitric Oxide in the Vasorelaxant and Hypotensive Effects of Extracts and Purified Tannins from Geum Japonicum," Journal of Ethnopharmacology, vol. 109, (2007), pp. 128-133.
Bhattachrya, Salil K. et al., "Effect of Bioactive Tannoid Principles of Emblica Officinalis on Ischemia-Reperfusion-Induced Oxidative Stress in Rat Heart," Phytomedicine, vol. 9, No. 2, Jan. 1, 2002, pp. 171-174.
Fogo, A.S et al., "Tormentic acid reduces vascular smooth muscle cell proliferation and survival," European Journal of Pharmacology, vol. 615, No. 1-3, Aug. 1, 2009, pp. 50-54.
Search Report issued in European Application No. 10785821.9 dated Feb. 15, 2013 (10 pages).
Search Report received in European Application No. 10785818.5 dated Feb. 19, 2013 (11 pages).
EUFICREVIEW, Web publication date: Nov. 1998 [Examiner retrieved from the internet on: Mar. 25, 2013], Retrieved from URL: http://www.eufic.org/article/en/expid/review-diet-lifestyle-life-expectancy/ (6 pages).
Non-Final Office Action issued for U.S. Appl. No. 13/377,501 mailed on Mar. 28, 2013 (17 pages).
Adams, K.F. et. al.,"Clinical benefits of low serum digoxin concentrations in heart failure," Jnl of Am College of Cardiology, (2002), vol. 39, No. 6, pp. 946-953.
Anderson, Koren J. et al., "Walnut Polyphenolics Inhibit in Vitro Human Plasma and LDL Oxication 1,2," Jnl of Nutrition, (2001), 131(11), pp. 2837-2842.
Bonfill, M. et al., "Identification of triterpenoid compounds of Centella asiatica by thin-layer chromatography and mass spectrometry," Biomedical Chromatography, (2005), 20(2), pp. 151-153.
Brinkhaus, B. et al., "Chemical, pharmacological and clinical profile of the East Asian medical plan Centella aslatica," Phytomedicine, (2000), vol. 7(5), pp. 427-448.
Definitions of "Ischemic Heart Disease" and "Coronary Heart Disease" from Hyperdictionary, retreived on Sep. 11, 2013 from http://hyperdictionary.com.
Fukuda, Toshiyuki et al., "Antioxidative polyphenols from walnuts (*Juglans regia* L.)," Phytochemistry, (2003), 63(7), pp. 795-801.
Lapornik, Brigita et al., "Comparison of extracts prepared from plant by-products using different solvents and extraction time," (2005), Jnl Food Engineering, 71(2), pp. 214-222.
Larrosa, Mar et al., "Ellagitannins, ellagic acid and vascular health," Molecular Aspects of Medicine, (2010), 31(6), pp. 513-539.
Meredith, Peter A. et al., "From Hypertension to Heart Failure—Are there better primary prevention strategies?," Jnl of Renin-Angiotensin-Aldosterone System, (Jun. 2006), vol. 7, No. 2, pp. 64-73.
Non-Final Office Action issued in U.S. Appl. No. 13/377,483 mailed Aug. 22, 2013 (27 pages).
Non-Final Office Action issued in U.S. Appl. No. 13/377,503 mailed Aug. 30, 2013 (28 pages).
Pragada, R.R. et al., "Carioprotective activity of Hydrocotyle asiatica L. in ischemia-reperfusion induced myocardial infarction in rats," Jnl of Ethnopharmacology, (2004), 93, pp. 105-108.
Turkmen, Nihal et al., "Effects of extraction solvents on concentration and antioxidant activity of black and black mate tea polyphenols determined by ferrous tartrate and Folin-Ciocalteu methods," (2006), Food Chemistry, 99(4), pp. 835-841.
Wojtczak, Dr. Andrzej, "Glossary of Medical Education Terms: 'Prevention'," (Feb. 2002), 5 pages.
Yoshida, Takashi et al., "Dimeric ellagitannins, laevigatins E, F and G from Rosa Laevigata," Phytochemistry, (1989), vol. 28, No. 9, pp. 2451-2454.
Final Office Action received in U.S. Appl. No. 13/377,483 mailed Mar. 28, 2014 (24 pages).
Final Office Action received in U.S. Appl. No. 13/377,503 mailed Apr. 2, 2014 (18 pages).
Yoshida, et al., "Tannins of Rosaceous Medicinal Plants. Part 2. Gemins A, B, and C, New Dimeric Ellagitannins from Geum japonicum", J. Chem. Soc. Perkin Trans. I, (1985), pp. 315-321.
Examination Report No. 1 received in Australian Patent Application No. 2010258358 issued Oct. 15, 2014, 5 pages.
Final Office Action received in U.S. Appl. No. 13/377,501 mailed Sep. 20, 2013 (12 pages).

(56) References Cited

OTHER PUBLICATIONS

Bhattacharya, Salil K. et al., "Effect of bioactive tannoid principles of Emblica officinalis on ischemia-reperfusion-induced oxidative stress in rat heart," Phytomedicine, (2002), vol. 9, pp. 171-174.
Dong-Sheng, Ming et al., "Research Progress in Chemical Constituents and Biological Activities of *Geum* Species," Acta Pharma, (2000), vol. 35, No. 7, pp. 552-558.
Office action received in Japanese Patent Application No. 2012-514548 issued Jun. 16, 2014, 7 pages, with English translation.
Office Action received in Japanese Patent Application No. 2012-514549 issued Jul. 2, 2014, 5 pages with English translation.
Office Action received in Japanese Patent Application No. 2012-514550 issued May 21, 2014, 6 pages with English translation.
Office Action received in Japanese Patent Application No. 2012-514551 issued Jun. 30, 2014, 9 pages with English translation.
Office Action received in Japanese Patent Application No. 2012-514552 issued May 26, 2014, 6 pages, with English translation.
Office Action received in Japanese Patent Application No. 2012-514554 issued May 28, 2014, 8 pages, with English Translation.
Patent Examination Report No. 1 received in Australian Patent Application No. 2010258351 issued Jul. 31, 2014, 4 pages.
Patent Examination Report No. 1 received in Australian Patent Application No. 2010258352 issued Jul. 7, 2014, 4 pages.
Patent Examination Report No. 1 received in Australian Patent Application No. 2010258354 issued Jul. 11, 2014, 3 pages.
Patent Examination Report No. 1 received in Australian Patent Application No. 2010258355 issued Jul. 31, 2014, 3 pages.
Final Office Action on U.S. Appl. No. 13/377,501, mailed Jul. 9, 2015.
Final Office Action on U.S. Appl. No. 13/377,503, mailed Jun. 29, 2015.
Ansel, Howard C. et al., Seventh Edition, Pharmaceutical Dosage Forms and Drug Delivery Systems, "Chapter 2: New Drug Development and Approval Process," (1999), 6 pages.
Non-Final Office Action received in U.S. Appl. No. 13/377,501 issued Jan. 2, 2015, 17 pages.
Non-Final Office Action received in U.S. Appl. No. 13/377,503 mailed Jan. 6, 2015, 28 pages.
Final Rejection on Japanese Application 2012-514550, mailed Feb. 2, 2015 (English translation included).
Lobmeyer et al., "Synergistic polymorphisms of Beta 1 and x2c-adrenegic receptors and the influence on left ventricular ejection fraction response to beta-blocker therapy in heart failure," Pharmacogenetics and genomics, 17, 2007, pp. 277-282.
Notice of Allowance on U.S. Appl. No. 13/377,483, mailed Feb. 11, 2015.
Office Action on Japanese Application 2012-514549, mailed Feb. 25, 2015, English translation provided.
Office Action on Japanese Application 2012-514551, mailed Feb. 23, 2015, English translation provided.
Office Action on Japanese Application 2012-514554, mailed Feb. 25, 2015, English translation provide.
Examination Report No. 2 on Australian Application 2010258354, issued Apr. 1, 2015.
Examination Report on Australian Application 2010258356, issued Apr. 2, 2015.
H.B. MacPhillamy: Drugs From Plants: Plant Science Bulletin, Botanical Society of America, vol. 9, No. 2, Apr. 1963, 15 pages.
MayoClinic: Alzheimer's Disease, from www.mayoclinic.com/health/alzheimers-diseas/DS00161/METHOD print&DSECTION all, Jan. 28, 2013, 15 pages.
Non-Final Office Action on U.S. Appl. No. 13/377,498, mailed Apr. 13, 2015.
Non-Final Office Action on U.S. Appl. No. 13/377,502, mailed Apr. 7, 2015.
Phillipson, J. "New Drugs From Nature—It Could Be Yew," Phytotherapy Research, 13, 1999, pp. 2-8.
Raskin et al., "Can an Apple a Day Keep the Doctor Away?" Current Pharmaceutical Design, 2004, 10, pp. 3419-3429.
Revilla et al., "Comparison of Several Procedures Used for the Extraction of Anthocyanins from Red Grapes,"J. Agric. Food Chem, 46, Oct. 29, 1998, pp. 3419-3429.
Smet et al., Herbal Remedies, The New England Journal of Medicine; vol. 347, Issue 25, Dec. 19, 2002, pp. 2046-2056.
Vickers et al., "A Vaccine Against Alzheimer's Disease,:" Drugs Aging, 19 (7), 2002, pp. 487-494.
Notice of Acceptance issued on Australian Application 2010258354, mailed Jul. 29, 2015.
Second Examination Report issued on Australian Application 2010258355, issued Aug. 5, 2015.

\* cited by examiner

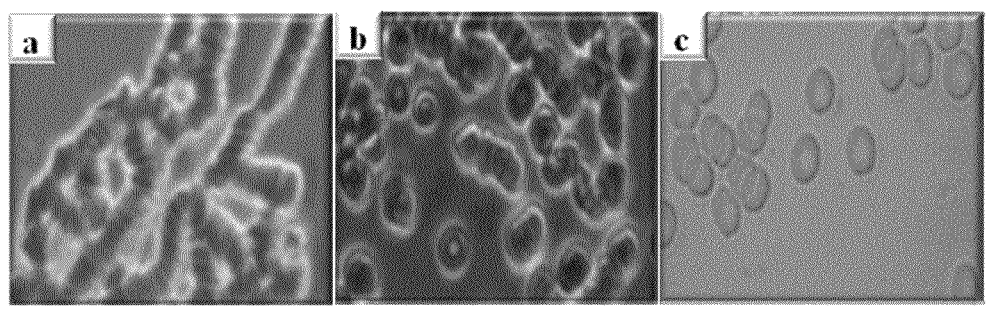

COMPOSITIONS AND METHODS FOR THE PREVENTION AND TREATMENT OF RED BLOOD CELL COAGULATION

CROSS-REFERENCE TO RELATED APPLICATIONS

The present application is the U.S. National Stage Application of PCT International Application No. PCT/IB2010/001415, filed Jun. 11, 2010, which claims priority to U.S. Provisional Application No. 61/186,709, filed Jun. 12, 2009, and U.S. Provisional Application No. 61/187,905, filed Jun. 17, 2009, the entire contents of which are hereby incorporated by reference in their entirety.

BACKGROUND

The following description is provided to assist the understanding of the reader. None of the information provided or references cited is admitted to be prior art to the present invention.

Red blood cell (RBC) aggregation has been widely studied and its importance is well established in the rheology of microcirculation (Aleksander S et al. 2005; E. Vicaut et al. 1994; J. J. Durussel et al. 1998). Three significant factors responsible for microcirculatory blood flow disorders are the increased RBC aggregation, increased plasma viscosity and lowered erythrocyte deformability (S Chien et al. 1987; G. Cicco et al. 1999; V. Nagaprasad et al. 1998). Under physiological conditions, the RBC in static or slowly moving blood can adhere to each other like piles of coins to form reversible cell-to-cell contact leading to formation of aggregates.

RBC aggregation increases blood viscosity and thus affects the passage of the cells through microvessels, especially in venules (Mark J et al. 2000; George Mchedlishvili et al. 2002). In pathological conditions, RBCs can form irreversible or less reversible aggregates, which are capable of plugging arterioles and venules. Abnormal RBC aggregation has been found to be associated with several diseases and conditions, including diabetes, malaria, heart failure, ischemic heart diseases, stroke, brain hypoperfusion, ischemic limbs, hypertension, hematological disorders, anesthesia and many others (John A et al. 1979; Amiram Eldor et al. 2002; Patricia foresto et al. 2000).

The RBC diameter is larger than the average diameter of capillary, and therefore RBCs must deform to pass through capillaries one at a time, in boxcar fashion. However, RBC aggregates are not able to pass through capillaries. Hence, extensive RBC aggregation would increase blood viscosity and reduce the effective blood perfusion of important organs and the whole body.

In normal blood, RBC aggregation is a reversible process in the presence of adequate shear forces. However, pathological RBC aggregation forms rapidly and extensively. Currently available therapeutic approaches or drugs can only offer relief of symptoms or slow down the progressive worsening of the condition. Effective separation of the aggregated RBC and prevention of RBC from further aggregation would significantly improve microcirculation that would further contribute to the effective prevention or treatment of many severe diseases, such as heart attack, stroke, ischemic heart diseases, heart failure, hypertension, ischemic limbs, brain hypoperfusion, and wound healing, especially in aged populations.

SUMMARY

This disclosure relates inter alia to methods of preventing RBC aggregation and restoring the irregularly aggregated erythrocytes in various pathological conditions into a regular and well-dispersed form that would reduce the viscosity of blood and subsequently improve microcirculation of organs and tissues of the body.

In one aspect, the present invention relates to a method of treating or preventing RBC coagulation in a mammalian subject in need thereof, comprising administering to the mammalian subject an effective amount of an organic extract of *Geum japonicum*. In one embodiment, the organic extract is an ethanol extract. In another embodiment, the organic extract is a methanol extract. In one embodiment, the subject is a human. In some embodiments, the RBC coagulation is associated with diabetics, malaria, heart failure, ischemic heart disease, stroke, brain hypoperfusion, ischemic limbs, hypertension, hematological disorders, or anesthesia.

In one embodiment, the extract of *Geum japonicum* is administered orally. In one embodiment, the extract of *Geum japonicum* is administered by subcutaneous injection, intramuscular injection, or intravenous infusion. In one embodiment, the extract is administered in an amount from about 0.01 mg/kg/day to about 10000 mg/kg/day. In one embodiment, the effective amount of the extract is in the form of a formulation comprising the extract and a pharmaceutically-acceptable carrier.

In another aspect, the present invention provides a pharmaceutical composition for inhibiting RBC coagulation in a mammalian subject comprising an effective amount of an organic extract of *Geum japonicum* and a pharmaceutically acceptable carrier. In one embodiment, the organic extract is an ethanol extract. In another embodiment, the organic extract is a methanol extract.

BRIEF DESCRIPTION OF THE FIGURES

FIG. 1 is a series of dark field phase contrast microscope images of representative live blood cell samples. Panel (a) is the blood sample obtained from the patient with dizziness, chest suppression and ischemia of the digits. The image shows tens or hundreds of the red cells aggregated forming various long rouleaux. Panel (b) is the blood specimen obtained from the same patient after one week treatment with the extract. The long rouleaux RBC aggregates were shortened with more than 50% of the red cells well dispersed. Panel (c) is the blood sample of the same patient 2 weeks after the extract treatment. Most of the red cells were well-dispersed and almost no rouleau-like RBC aggregates were observed.

DETAILED DESCRIPTION

In various aspects, the present invention provides compounds, extracts, and methods for preventing or treating RBC coagulation and diseases associated with abnormal RBC aggregation. The compounds provided herein can be formulated into pharmaceutical compositions and medicaments that are useful in the disclosed methods. Also provided are the use of the compounds and extracts in preparing pharmaceutical formulations and medicaments.

It is to be appreciated that certain aspects, modes, embodiments, variations and features of the invention are described below in various levels of detail in order to provide a substantial understanding of the present invention. The following terms are used throughout as described below, unless context clearly indicates otherwise.

As used herein, the "administration" of an agent or drug to a subject or subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another. It is also to be appreciated that the various modes of treatment or prevention of medical conditions as described are intended to mean "substantial", which includes total but also less than total treatment or prevention, and wherein some biologically or medically relevant result is achieved.

As used herein, the term "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with a disease that is being treated. The amount of a composition of the invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds.

The abbreviation "OEGJ" used in the invention, without specific indication, means an extract of the plant Geum japonicum by an organic solvent described below.

As used herein, the term "subject" refers to a mammal, such as a human, but can also be an animal, e.g., domestic animals (e.g., dogs, cats and the like), farm animals (e.g., cows, sheep, pigs, horses and the like) and laboratory animals (e.g., monkey, rats, mice, rabbits, guinea pigs and the like).

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for a disorder if, after receiving a therapeutic agent according to the methods of the present invention, the subject shows observable and/or measurable reduction in or absence of one or more signs and symptoms of a particular disease or condition.

As used herein, "prevention" or "preventing" of a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

Compositions of the Invention

In some embodiments, the compound is a whole plant, an extract, e.g., an organic extract, of Geum japonicum, Xian he cao, Agrimonia pilosa Ledeb. (Rosaceae); and Thymus mongolicus Ronn (Lamiaceae). In a particular embodiment, the compound is a methanol/ethanol extract of Geum japonicum or an active fraction thereof. In some embodiments, the compound is a fraction of an extract of Geum japonicum.

The present invention provides methods of treating or preventing a variety of diseases or medical conditions with agents and/or extracts and compounds, and derivatives of such compounds from a variety of plants including Geum japonicum. In some embodiments, the agent is an extract, e.g., an organic extract, of Geum japonicum. In a particular embodiment, the agent is a methanol/ethanol extract of Geum japonicum or an active fraction thereof.

A method for preparing an organic extract from Geum japonicum is provided. This method comprises the step of (a) extracting the plant of Geum japonicum with alcohol selected from the group consisting of C1-C4 alcohols. This step may be repeated 3-6 times, typically 5 times, at room temperature. Before performing step (a), the plant material may be powdered or cut into small pieces. The C1-C4 alcohols include methanol, ethanol, n-propanol, iso-propanol, n-butanol, iso-butanol, and ter-butanol. Typically, alcohol is added in 1-10 times by weight of the amount of the Geum japonicum to be extracted.

The methods may further comprise the step of (b) drying the extract obtained from the step of (a) into a dried powder; and (c) successively extracting the powder obtained from the step of (b) with C6 alkane, EtOAc and an alcohol selected from the group consisting of C1-C4 alcohols. The C6 alkane includes cyclic and non-cyclic alkane having 6 carbon atoms, including, for example, cyclohexane, n-hexane, and neo-hexane, etc. The C1-C4 alcohols include methanol, ethanol, n-propanol, iso-propanol, n-butanol, iso-butanol, and ter-butanol. The amount of organic solvent to be used is typically 1-10 times by weight of the amount of the powders or small pieces to be further extracted.

The method as recited above may also include filtering the extract to remove any insoluble powders therein. A drying step may be completed under reduced pressure at a temperature higher than room temperature, for example, at 50° C. or by electro-spray.

To purify the OEGJ, the method may further comprise the steps of applying the powder to a chromatographic column; and eluting the column with an aqueous solution with increasing concentration of an alcohol selected from the group consisting of C1-C4 alcohols. For example, a Sephadex or reverse phase column may be used. The alcohol used may be any one selected from the group consisting of methanol, ethanol, n-propanol, iso-propanol, n-butanol, iso-butanol, and ter-butanol.

By NMR analysis, it is found that the OEGJ typically contains mainly tannins including gemin A, B, C, D, E and F and triterpenes including 2-hydroxyoleanolic acid, 2-hydroxylursolic acid, 2,19-dihydroxy-ursolic acid, 2-α,19-α-dihydroxy-3-oxo-12-ursen-28-oic acid, ursolic acid, epimolic acid, maslinic acid, euscaphic acid, tormentic acid, 28-β-D-glucoside of tormentic acid.

In one embodiment, the extracts, fractions, and compounds of the invention are obtained by extraction, using water and/or of an organic solvent, from crude plant material comprises the following stages:
1. Extraction by addition to the plant material, of water and/or of organic solvent(s), by subjecting the whole to a treatment such as maceration/lixiviation, ultrasonics or microwaves;
2. Delipidation before or after the extraction stage using a solvent of petroleum ether, hexane or chloroform type;
3. Optionally, additional extraction of the extract recovered by an organic solvent of ethyl acetate or ethyl ether type,
4. Optionally, concentration of the crude extract obtained, and, if desired, its lyophilization.

According one aspect, considering the enrichment that it allows to be attained, the crude extract may be subjected to a purification stage by chromatography. In one embodiment, centrifugal partition chromatography (CPC) is used. This technique is in particular described by A. P. FOUCAULT, Ed., Centrifugal Partition Chromatography, Chromatographic Science Series, Marcel Dekker Inc., 1995, 68, or W. D. CONWAY, Ed., Countercurrent Chromatography apparatus theory and applications, VCH Publishers Inc., 1990. CPC is based on the partition of the solutes between two non-miscible liquid phases prepared by the mixture of two or more solvents or solutions. One of the two phases is kept stationary by a centrifugal force. The solvents, their proportions and the flow rate chosen closely depend both on the stability of the stationary phase within the CPC column and the actual pressure.

A person skilled in the art will therefore choose the most appropriate solvent or solvents depending on the nature of the purified extract desired. These different extracts, namely crude or enriched also fall within the scope of the invention. The implementation of additional separation stages allows isolation of these extracts enriched with one or more compounds. These separations can be carried out on fractions enriched from a crude extract or on the crude extract itself by using mixtures of appropriate solvents according to the proportions which are suitable for the sought separation.

Methods for Treating and Preventing Red Blood Cell Coagulation and Related Disorders Pathological RBC aggregation is a high-risk and potentially lethal symptom that is frequently accompanied with aging, high-calorie diets and cardiocerebrovascular diseases. It starts with aggregation of 3-10 or more red cells. When the aggregated RBC cluster is too big to pass through a capillary, it results in impaired delivery of oxygen or even blockage of blood vessels that may cause cerebral embolism, heart attack, pulmonary embolism and peripheral embolism. If this happens in vital region of the body, it could cause severe functional loss, or may even be life-threatening.

Currently available blood thinners, such as Warfarin, act by inhibiting the synthesis of clotting factors, thus preventing blood clot formation. However, these blood thinners do not affect RBC aggregation. Microvascular occlusion by RBC aggregates has been reported in several conditions, including diabetic retinopathy, leg vein thrombosis, chronic venous insufficiency, retinal vein occlusion, limb end ischemia and macroglobulinemia. The aggregates take the form of rouleaux, which may be sufficiently big in size to occlude small vessels. The causative factor for the aggregation depends on the specific disease entity. Treatment of RBC aggregation-induced occlusion with heparin, warfarin, prednisone, and vasodilators will not provide any relief. Therefore, there is a substantial demand for drugs of preventing and treating pathological RBC aggregations.

In one aspect, the present disclosure relates to an organic extract of *Geum japonicum* that can restore the irregularly aggregated erythrocytes into regular and discrete forms that reduce the viscosity of the blood and subsequently improve microcirculation of the whole body. Abnormal RBC aggregation may lead to the formation of irregular aggregate structures, which may be induced by cell-associated factors (reduced membrane sialic acid levels) but also by extracellular factors. Increased RBC aggregation has been observed in several pathological states. For example, increased aggregation of RBCs resulted from a decreased sialylation of glycophorins may be an important factor in the development of vascular diseases and in the microcirculation impairment. As such, the present disclosure provides methods for the treatment or prevention of vascular diseases in mammalian subjects by administering to the subject an effective amount of the OEGJ.

In one embodiment, the deaggregation effect of the compositions of the invention on the aggregated RBC reduces blood viscosity, and substantially improves the microcirculation and effective blood perfusion of the body. In one embodiment, the extract prevents RBC aggregation, which in turn, prevents heart attack, stroke (brain attack), hypertension, cerebrocardiovascular ischemia and impaired microcirculation-related diseases, such as limb ischemia, etc. In one embodiment, the deaggregation effect of the extract increases effective blood perfusion and improves microcirculation for the treatment of disease. Accordingly, the present invention provides anticoagulation and antithrombotic treatments aimed at inhibiting the formation of blood clots in order to prevent or treat blood coagulation disorders, such as myocardial infarction, stroke, loss of a limb by peripheral artery disease or pulmonary embolism.

In one embodiment, plants, extracts, active fractions, and/or compounds of the invention may be administered as part of a combination therapeutic with a vasodilator agent, e.g., bencyclane, cinnarizine, citicoline, cyclandelate, cyclonicate, ebumamonine, phenoxezyl, flunarizine, ibudilast, ifenprodil, lomerizine, naphlole, nikamate, nosergoline, nimodipine, papaverine, pentifylline, nofedoline, vincamin, vinpocetine, vichizyl, pentoxifylline, prostacyclin derivatives (such as prostaglandin E1 and prostaglandin I2), an endothelin receptor blocking drug (such as bosentan), diltiazem, nicorandil, and nitroglycerin.

In one embodiment, plants, extracts, active fractions, and/or compounds of the invention may be administered as part of a combination therapeutic with another anticoagulant, a thrombolytic drug, or an antihypertensive agent. Examples of the anticoagulant include heparins (such as heparin sodium, heparin potassium, dalteparin sodium, dalteparin calcium, heparin calcium, pamaparin sodium, reviparin sodium, and danaparoid sodium), warfarin, enoxaparin, argatroban, batroxobin, and sodium citrate. Examples of the antiplatelet drug include ticlopidine hydrochloride, dipyridamole, cilostazol, ethyl icosapentate, sarpogrelate hydrochloride, dilazep hydrochloride, trapidil, a nonsteroidal antiinflammatory agent (such as aspirin), beraprostsodium, iloprost, and indobufene. Examples of the thrombolytic drug include urokinase, tissue-type plasminogen activators (such as alteplase, tisokinase, nateplase, pamiteplase, monteplase, and rateplase), and nasaruplase. Examples of the antihypertensive drug include angiotensin converting enzyme inhibitors (such as captopril, alacepril, lisinopril, imidapril, quinapril, temocapril, delapril, benazepril, cilazapril, trandolapril, enalapril, ceronapril, fosinopril, imadapril, mobertpril, perindopril, ramipril, spirapril, and randolapril), angiotensin II antagonists (such as losartan, candesartan, valsartan, eprosartan, and irbesartan), calcium channel blocking drugs (such as aranidipine, efonidipine, nicardipine, bamidipine, benidipine, manidipine, cilnidipine, nisoldipine, nitrendipine, nifedipine, nilvadipine, felodipine, amlodipine, diltiazem, bepridil, clentiazem, phendilin, galopamil, mibefradil, prenylamine, semotiadil, terodiline, verapamil, cilnidipine, elgodipine, isradipine, lacidipine, lercanidipine, nimodipine, cinnarizine, flunarizine, lidoflazine, lomerizine, bencyclane, etafenone, and perhexiline), β-adrenaline receptor blocking drugs (propranolol, pindolol, indenolol, carteolol, bunitrolol, atenolol, acebutolol, metoprolol, timolol, nipradilol, penbutolol, nadolol, tilisolol, carvedilol, bisoprolol, betaxolol, celiprolol, bopindolol, bevantolol, labetalol, alprenolol, amosulalol, arotinolol, befunolol, bucumolol, bufetolol, buferalol, buprandolol, butylidine, butofilolol, carazolol, cetamolol, cloranolol, dilevalol, epanolol, levobunolol, mepindolol, metipranolol, moprolol, nadoxolol, nevibolol, oxprenolol, practol, pronetalol, sotalol, sufinalol, talindolol, tertalol, toliprolol, xybenolol, and esmolol), α-receptor blocking drugs (such as amosulalol, prazosin, terazosin, doxazosin, bunazosin, urapidil, phentolamine, arotinolol, dapiprazole, fenspiride, indoramin, labetalol, naftopidil, nicergoline, tamsulosin, tolazoline, trimazosin, and yohimbine), sympathetic nerve inhibitors (such as clonidine, guanfacine, guanabenz, methyldopa, and reserpine), hydralazine, todralazine, budralazine, and cadralazine.

Formulations and Dosages of Pharmaceutical Compositions.

In various embodiments of the invention, suitable in vitro or in vivo assays are performed to determine the effect of an agent (extracts, fractions and compounds) of the invention and whether its administration is indicated for treatment of the affected disease or medical condition in a subject.

Typically, an effective amount of the compositions of the present invention, sufficient for achieving a therapeutic or prophylactic effect, range from about 0.000001 mg per kilogram body weight per day to about 10,000 mg per kilogram body weight per day. Suitably, the dosage ranges are from about 0.01 mg per kilogram body weight per day to 2,000 mg per kilogram body weight per day. An exemplary treatment regime entails administration once every day or once a week or once a month. The agent usually administered on multiple occasions. Intervals between single dosages can be daily, weekly, monthly or yearly. Alternatively, the agents can be administered as a sustained release formulation, in which case less frequent administration is required. Dosage and frequency vary depending on the half-life of the agent in the subject. The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the patent can be administered a prophylactic regime.

Toxicity.

Suitably, an effective amount (e.g., dose) of an agent described herein will provide therapeutic benefit without causing substantial toxicity to the subject. Toxicity of the agent described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the agent described herein lies suitably within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics*, Ch. 1 (1975).

According to the methods of the present invention, the agents can be incorporated into pharmaceutical compositions suitable for administration. In some embodiments, the pharmaceutical compositions may comprise purified or substantially purified extracts of *Geum japonicum* and a pharmaceutically-acceptable carrier in a form suitable for administration to a subject. In other embodiments, the pharmaceutical compositions may comprise pharmaceutically-acceptable carriers are determined in part by the particular composition being administered, as well as by the particular method used to administer the composition. Accordingly, there are a wide variety of suitable formulations of pharmaceutical compositions for administering the compositions (see, e.g., *Remington's Pharmaceutical Sciences*, Mack Publishing Co., Easton, Pa. 18$^{th}$ ed., 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. A person of ordinary skill in the art, would have no difficulty determining the appropriate timing, sequence and dosages of administration for particular drugs and compositions of the present invention.

Suitable examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the agent, use thereof in the compositions is contemplated. Supplementary active compounds can also be incorporated into the compositions.

A pharmaceutical composition of the invention is formulated to be compatible with its intended route of administration. The compositions of the present invention can be administered by parenteral, topical, intravenous, oral, subcutaneous, intraarterial, intradermal, transdermal, rectal, intracranial, intraperitoneal, intranasal; intramuscular route or as inhalants. The agent can optionally be administered in combination with other agents that are at least partly effective in treating various diseases.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating the agents in the required amount in an appropriate solvent with one or a combination of ingredients enumerated above, as required, followed by filtered sterilization. Generally, dispersions are prepared by incorporating the binding agent into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The agents of this invention can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the binding agent can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

In one embodiment, the agents are prepared with carriers that will protect the agent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

EXAMPLES

The present technology is further illustrated by the following examples, which should not be construed as limiting in any way.

Example 1

Preparation of an Active Composition for Preventing and Treating RBC Aggregation This example describes the identification and preparation of an active composition that prevents RBCs from aggregating and separates already aggregated RBCs into a well dispersed cell population. A bio-assay guided strategy was used for screening plant constituents to identify the composition of compounds showing these actions. During the screening process, an active fraction isolated from *Geum japonicum Thumb.* var. was identified to effectively prevent RBC from aggregation and to substantially separate the RBC aggregates into well-dispersed cells.

Briefly, adult *Geum japonicum* was collected in July from Huangshan and dried. The dried plant was cut into small pieces, and percolated with 75% ethanol (10× volumes) at room temperature for 6 days. The extract was electro-sprayed to yield brown powder.

Example 2

Treatment of RBC Aggregation in Human Subjects

In this Example, we tested the therapeutic effect of the extract on patients with RBC aggregation with their consent in a clinical setting. The patient was 58 years old who had dizziness and chest suppression and a sudden onset of cyanosis and pain in the fingers. The patient had no history of diabetes, Raynaud's phenomenon or cold intolerance. Physical examination revealed cyanosis of the distal digits of the patient's fingers. Microscopic examination of the patient's peripheral blood smears revealed a severe degree of RBC aggregation in the form of long rouleaux chains composed of 10-100 RBCs in each chain or clump (FIG. 1A). The patient felt headache, chest suppression, dizziness, coldness of the fingers and failed to respond to the traditional blood thinner treatment.

The first patient was then treated with the extract of Example 1 (orally, 3 grams/day) for two weeks with his full consent. One week after treatment, instead of rouleaux formation with long chains of red cells composed of 10 to 100 RBCs in each chain, the aggregates were composed of only short chains of rouleaux of 2 to 10 red cells in each aggregate with many well-dispersed red cells (FIG. 1B). Furthermore, treatment of the patient for two weeks with the extract completely dispersed the RBC aggregates and almost all red cells were well separated with almost no RBC aggregates observed (FIG. 1C). The two-week treatment with the extract led to a prompt relief of the ischemic symptoms of the patient, such as the dizziness, headache and chest suppression, with a return of color and warmness to his digits. Namely, the reduction in RBC aggregation had resulted in a reduced blood viscosity and increased effective blood perfusion and oxygenation to all the organs and tissues of the patient, as indicated by the improved blood perfusion to his end extremities and significantly improved symptoms.

Three other male patients (55-65 years old) reported dizziness, chest suppression, ischemic limbs and blood hyperviscous. On examination of their peripheral blood smear with dark field phase contrast microscope, it revealed significant degrees of RBC aggregation (Table 1). They were then treated following the same protocol (3 g/day for 2 weeks) with their full consent. Similar treatment effects to the first patient were achieved. The rouleaux RBC aggregates were significantly shortened one week after treatment and the red cells were further well dispersed and almost no red cell aggregations were observed after two weeks of treatment with the extract (Table 1). The underlying mechanism for the prompt relief of the symptoms of the patients is probably due to the reduced viscosity of the blood as a result of the substantially reduced RBC aggregation. The abnormal RBC aggregation with marked rouleaux formation probably contributed to the patients' digital ischemia, dizziness and chest suppression.

These results show that the the treatment of the patients with the active extract of Example 1 significantly reduced the RBC aggregation in the blood of the patients. As a result, the blood hyperviscosity was reduced, which would further help increase the effective blood perfusion and oxygen-carrying ability of the RBCs. The reduced blood viscosity and well dispersed RBC would increase the total number of the RBCs that can traverse the capillaries. We believe RBC aggregation increases the viscosity of blood at low shear rates and such an increased viscosity would enhance the flow stagnation and tendency to thrombosis.

Therefore, the OEGJ is found very useful in treating many microcirculation-associated diseases or conditions, such as cerebral hypoperfusion or ischemia, ischemic heart diseases, pulmonary embolism, venous embolism, peripheral ischemia, heart failure, limb ischemia (Raynaud's phenomenon), diabetic neuropathy, and chronic skin ulcerations. Hence, the extract is useful for the treatment of a variety of microcirculation-associated diseases mentioned above.

TABLE 1

| Symptoms | Before treatment | After treatment |
|---|---|---|
| Dizziness | +++ to ++++ | − |
| Chest suppression | + to ++ | − |
| Digital ischemia | ++ to +++ | − |
| Blood hyperviscous | +++ to ++++ | − to + |
| RBC aggregation | +++ to ++++ | − |

While certain-embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 units refers to groups having 1, 2, or 3 units. Similarly, a group having 1-5 units refers to groups having 1, 2, 3, 4, or 5 units, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERENCES

Aleksander S. Popel, Paul C. Johnson (2005) Microcirculation and hemorheology. *Annual Review of Fluid Mechanics*, Vol. 37: 43-69.

Amiram Eldor, Eliezer A. Rachmilewitz (2002) The hypercoagulable state in thalassemia. *Blood*, Vol. 99, No. 1, pp. 36-43.

E. Vicaut, X. Hou, L. Decuypère, A. Taccoen, M. Duvelleroy (1994) Red Blood Cell Aggregation and Microcirculation in Rat Cremaster Muscle, *Int J Microcirc*. 14:14-21.

G. Cicco, A. Pirrelli (1999) Red blood cell (RBC) deformability, RBC aggregability and tissue oxygenation in hypertension, *Clinical Hemorheology and Microcirculation*, 169-177.

G. Mchedlishvili, M. Varazashvili, L. Gobejishvili (2002) Local RBC aggregation disturbing blood fluidity and causing stasis in microvessels, *Clinical Hemorheology and Microcirculation*, 2: 99-106.

J. J. Durussel, M. F. B. G. Guiffant, J. Dufaux (1998) Effects of red blood cell hyperaggregation on the rat microcirculation blood flow, *Acta Physiol Scand*. 163(1):25-32.

J. A. Colwell, P. V. Halushka, K. E. Sarji, M. F. Lopes-Virella, Julius Sagel (1979) Vascular Disease in Diabetes, *Arch Intern Med*. 139(2):225-230.

M. J. Pearson, H. H. Lipowsky (2000) Influence of erythrocyte aggregation on leukocyte margination in postcapillary venules of rat mesentery, *Am J Physiol Heart Circ Physiol*. 279: H1460-H1471.

P. foresto, M. D'arrigo, l. carreras, R. E. Cuezzo, J. valverde, R. Rasia (2000) Evaluation of red blood cell aggregation in diabetes by computerized image analysis, *MEDICINA*, 60:570-572.

S Chien (1987) Red Cell Deformability and its Relevance to Blood Flow, *Annual Review of Physiology*, Vol. 49: 177-192.

V. Nagaprasad, M. Singh (1998) Sequential analysis of the influence of blood storage on aggregation, deformability and shape parameters of erythrocytes, *Clinical Hemorheology and Microcirculation*, 273-284.

What is claimed is:

1. A method of treating pathological red blood cell (RBC) aggregation in a mammalian subject in need thereof, comprising administering to the mammalian subject an effective amount of an organic extract of *Geum japonicum*.

2. The method of claim 1, wherein the organic extract is an ethanol extract.

3. The method of claim 1, wherein the organic extract is a methanol extract.

4. The method of claim 1, wherein the subject is a human.

5. The method of claim 1, wherein the extract of *Geum japonicum* is administered orally.

6. The method of claim 1, wherein the extract of *Geum japonicum* is administered by subcutaneous injection, intramuscular injection, or intravenous infusion.

7. The method of claim 1, wherein the extract is administered in an amount from 0.01 mg/kg/day to 10000 mg/kg/day.

8. The method of claim 1, wherein the effective amount of the extract is in the form of a formulation comprising the extract and a pharmaceutically acceptable carrier.

9. The method of claim 1, wherein the pathological RBC aggregation causes defects in microcirculation.

10. The method of claim 1, wherein the subject has one or more symptoms associated with pathological RBC aggregation.

11. The method of claim 10, wherein the one or more symptoms associated with pathological RBC aggregation comprise headache, dizziness, chest suppression, coldness of the digits, pain in the digits, cyanosis of the digits, ischemic limbs, hyperviscous blood, and lack of responsiveness to blood thinner treatment.

* * * * *